United States Patent
Bae et al.

(10) Patent No.: US 7,227,641 B2
(45) Date of Patent: Jun. 5, 2007

(54) METHOD AND APPARATUS FOR MEASURING A PITCH OF STRANDED CABLE

(75) Inventors: Sang-Joon Bae, Gyeonggi-do (KR); Young-Gyu Yaung, Gyeonggi-do (KR)

(73) Assignee: LS Cable, Ltd., Seoul (KR)

( * ) Notice: Subject to any disclaimer, the term of this patent is extended or adjusted under 35 U.S.C. 154(b) by 345 days.

(21) Appl. No.: 10/859,502

(22) Filed: Jun. 1, 2004

(65) Prior Publication Data

US 2005/0002036 A1    Jan. 6, 2005

(30) Foreign Application Priority Data

Jul. 1, 2003    (KR) ............... 10-2003-0044385

(51) Int. Cl.
*G01N 21/84*    (2006.01)
(52) U.S. Cl. ...................... 356/429; 356/430
(58) Field of Classification Search ............ None
See application file for complete search history.

(56) References Cited

U.S. PATENT DOCUMENTS 3,985,451 A * 10/1976 Plockl .................. 356/429
4,887,155 A * 12/1989 Massen ................... 348/88
5,990,468 A * 11/1999 Cornuejols ............ 250/208.1
6,837,074 B2 * 1/2005 Cocchini et al. ........... 65/382

FOREIGN PATENT DOCUMENTS

FR          2594534      *  1/1986

* cited by examiner

*Primary Examiner*—Michael P. Stafira
(74) *Attorney, Agent, or Firm*—Jones Day (57) ABSTRACT

Disclosed is a method for measuring a pitch of a stranded cable which includes the steps of (A) manufacturing a stranded cable by stranding at least two wires; (B) irradiating a parallel ray on one side of the stranded cable moving at a regular velocity, and receiving the parallel ray at the opposed side of the stranded cable; and (C) determining a stranded cycle of the cable on the basis of a light-receiving quantity pattern on the opposed side corresponding to a stranded pattern of the cable, and then measuring a stranded pitch of the cable by calculating a moved distance of the cable during the stranded cycle.

This method enables to measure a pitch of a spirally stranded cable in real time at a low cost.

14 Claims, 6 Drawing Sheets

| ROTATION MODE | W | W | W | W | W | W | W | W | W |
|---|---|---|---|---|---|---|---|---|---|
| | d | d(1+sin45°) | 2d | d(1+sin45°) | d | d(1+sin45°) | 2d | d(1+sin45°) | d |

METHOD AND APPARATUS FOR MEASURING A PITCH OF STRANDED CABLE

BACKGROUND OF THE INVENTION

1. Field of the Invention

The present invention relates to method and apparatus for measuring a pitch of a stranded cable, and more particularly to method and apparatus capable of measuring a pitch for a spirally stranded structure of a cable in real time at a low cost.

1. Description of the Related Art

A communication cable is generally manufactured by stranding at least two wires. At this time, it is important to strand the wires at regular pitches along a longitudinal direction in order to improve transition characteristics especially Near End Cross-Talk (NEXT) and Return Loss (RL).

Figure 1:
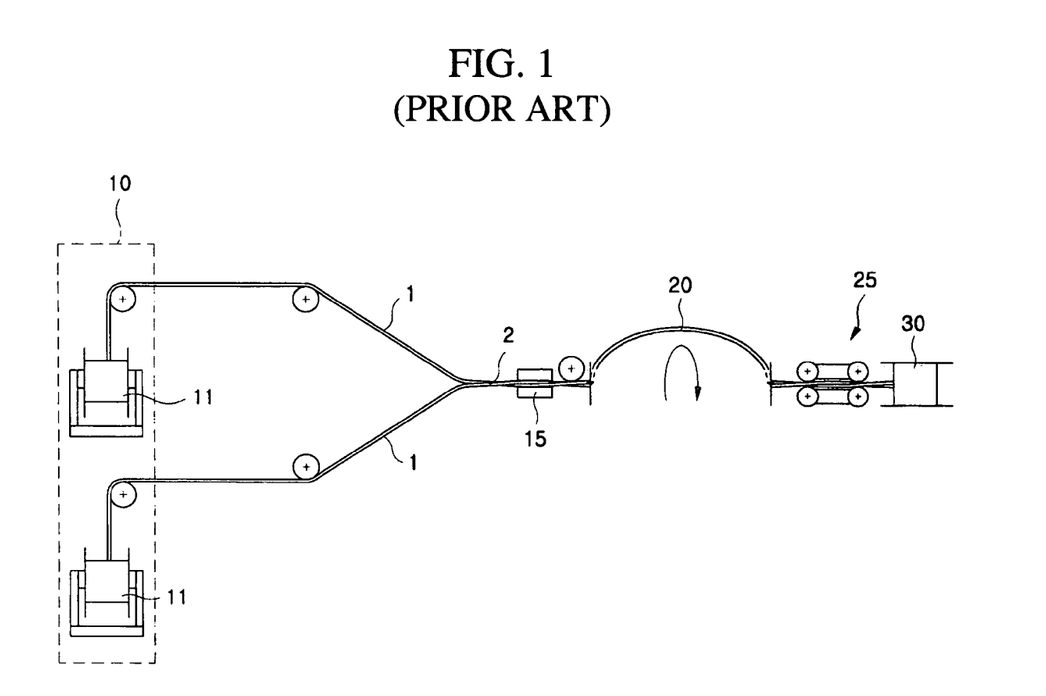
FIG. 1 is a schematic view showing an apparatus for manufacturing a stranded cable according to a conventional art.

FIG. 1 is a schematic view showing a conventional apparatus for manufacturing a stranded cable 2.

Referring to FIG. 1, the apparatus for manufacturing a stranded cable includes a wire pay-off 10 having a wire bobbin 11 for supplying at least two wires 1, a capstan 25 for drawing the wires 1 at a regular velocity, a guide die 15 and a rotation body 20 positioned between the wire pay-off 10 and the capstan 25, and a take-up device 30 for taking up the stranded cable 2.

The wires 1 continuously supplied from the wire pay-off 10 by drawing of the capstan 25 is transmitted to the take-up device 30 after being stranded through the rotation body 20 in a state of being collected by the guide die 15.

A method for manufacturing a stranded cable by using the conventional apparatus may be classified into, for example, single twister method, double twister method, triple twister method and so on according to the number of pitches per one rotation of the rotation body 20.

Here, it is important to accurately monitor a length of pitch in real time during the stranding process so as to generate regular pitchs along a longitudinal direction of the cable. However, since a means for measuring a pitch of a cable by an in-line method has not been provided in the past, a pitch was generally measured off-line after all processes are finished.

In the off-line method, since the pitch is measured with the naked eye by using a length measurement means such as a micrometer or a vernier calipers, the method has disadvantages that measurement time is too long, and a measurement value error is apt to be generated depending on persons in charge of the measurement.

On the other hand, since inferiority of the pitch generated during stranding process cannot be detected in real time, the conventional method has a disadvantage that operating conditions affecting on the pitch state cannot be adequately set. For example, in the fact that a pitch of the cable is continuously changed by a change of tensile force acted on the wire and a change of a ratio of wire-velocity to the rotation body frequency caused by a slip of the wire in the capstan 25, and so on, the conventional method cannot monitor these changes in real time.

SUMMARY OF THE INVENTION

The present invention is designed to solve the problems of the prior art, and therefore an object of the present invention is to provide method and apparatus for rapidly measuring a pitch of a spirally stranded cable in real time at a low cost.

In order to accomplish the object, the present invention provides a method for measuring a pitch of a stranded cable according to one embodiment of the present invention, which includes the steps of (A) manufacturing a stranded cable by stranding at least two wires; (B) irradiating a parallel ray on one side of the stranded cable moving at a regular velocity, and receiving the parallel ray at the opposed side of the stranded cable; and (C) determining a stranded cycle of the cable on the basis of a light-receiving quantity pattern on the opposed side corresponding to a stranded pattern of the cable, and then measuring a stranded pitch of the cable by calculating a moved distance of the cable during the stranded cycle.

At this time, a width of the parallel ray irradiated on one side of the cable should be set at least wider than a diameter of the cable.

In addition, the step (C) includes the steps of (a) generating a light-receiving signal in a shape of non-sinusoidal periodic wave corresponding to a light-receiving quantity on the opposed side; (b) converting the light-receiving signal into a square wave signal; (c) dividing the square wave signal into two parts; and (d) measuring a moved distance of the cable by using the divided square wave signal as a trigger signal.

Futhermore, the step (c) may include the steps of preparing a guide roller rotating in accordance with movement of the cable and an encoder for counting the rotation of the guide roller; counting the number of pulses output from the encoder by using the divided square wave signal as a trigger signal; and calculating a pitch P using the following equation, $$P = \frac{\pi D}{n} \times N$$

where P: a stranded pitch, π: the ratio of the circumference of a circle to its diameter, D: a diameter of the guide roller, n: the number of pulses of the encoder per one rotation, and N: the number of pulses of the encoder.

In another embodiment of the present invention, an apparatus for measuring a pitch of a stranded cable includes a stranded cable in which at least two wires are stranded in a predetermined pitch, a light-emitting element and a light-receiving element positioned on both opposite sides of the stranded cable moving in a predetermined direction, a measurement sensor for sensing a moved distance of the cable, and a pitch calculator for calculating a pitch of the stranded cable on the basis of an output value of the measurement sensor by using periodical change of the output signal from the light-receiving element as a trigger signal.

The measurement sensor includes a guide roller contacted with the cable for rotating as much as a moved distance of the cable, and an encoder for counting the rotation of the guide roller.

In addition, the pitch calculator includes a comparator for converting a light quantity signal output from the light-receiving element into a square wave, a frequency divider for dividing the square wave output from the comparator into two parts, and a signal processor for calculating a pitch of the stranded cable by counting the number of pulses of the encoder until the divided square wave is triggered.

At this time, the signal processor calculates a pitch of the stranded cable on the basis of the following equation, $$P = \frac{\pi D}{n} \times N$$

where P: a stranded pitch, π: the ratio of the circumference of a circle to its diameter, D: a diameter of the guide roller, n: the number of pulses of the encoder per one rotation, and N: the number of pulses of the encoder.

BRIEF DESCRIPTION OF THE DRAWINGS

Other objects and aspects of the present invention will become apparent from the following description of embodiments with reference to the accompanying drawing in which.

DESCRIPTION OF THE PREFERRED EMBODIMENT

Hereinafter, preferred embodiments of the present invention will be described in detail referring to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 2:
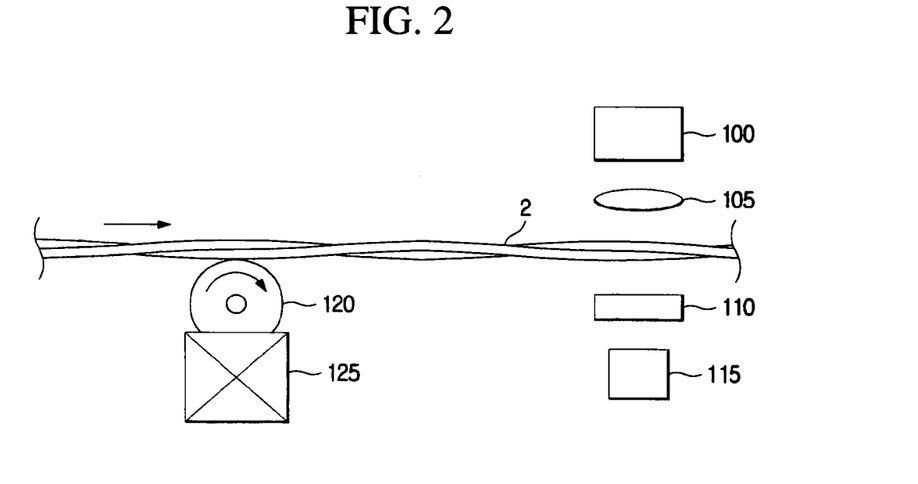
FIG. 2 is a schematic view showing an apparatus for measuring a pitch of a stranded cable according to a preferred embodiment of the present invention.

FIG. 2 is a schematic view showing an apparatus for measuring a pitch of a stranded cable according to a preferred embodiment of the present invention.

Referring to FIG. 2, the pitch measuring apparatus of the present invention includes a light-emitting unit 100 and a light-receiving unit 115 positioned on both opposite sides of a stranded cable 2, which is continuously progressed, a guide roller 120 and an encoder 125 operating in contact with the stranded cable 2, and a signal processor 155 (see FIG. 6) for calculating a pitch of the cable 2.

Figure 3:
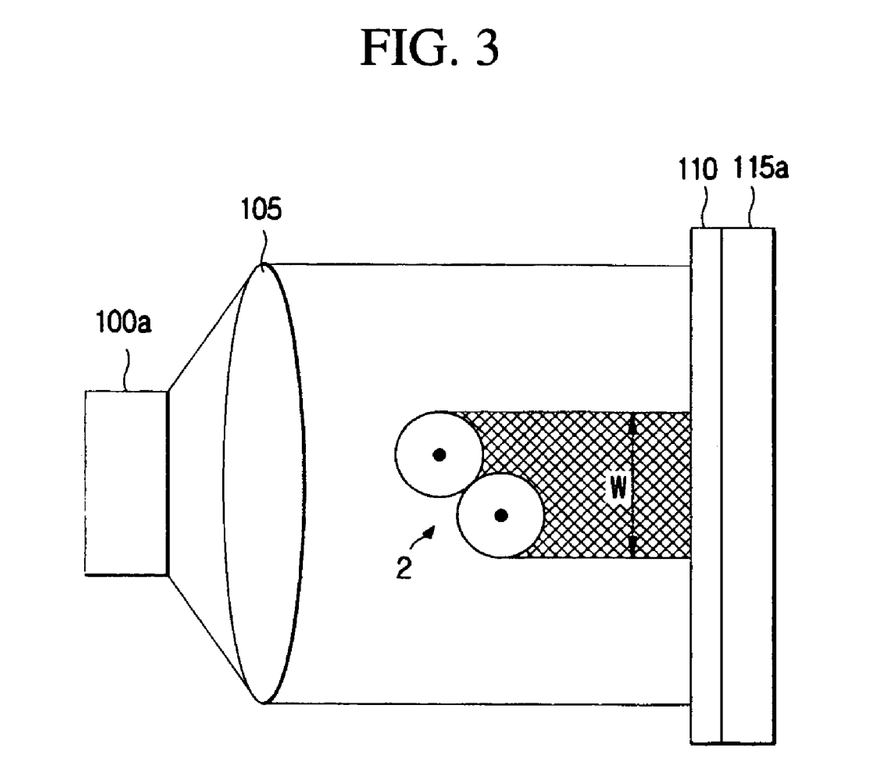
FIG. 3 is a sectional view showing that a light-receiving area is partially hidden by the cable in FIG. 2.

Since the stranded cable 2 is moved between the light-emitting unit 100 and the light-receiving unit 115, an irradiated ray emitted from the light-emitting unit 100 toward the light-receiving unit 115 reaches the light-receiving unit 115 in a state of being partially hidden as much as a portion corresponding to a spirally stranded structure of the cable 2, as shown in FIG. 3.

Figure 4:
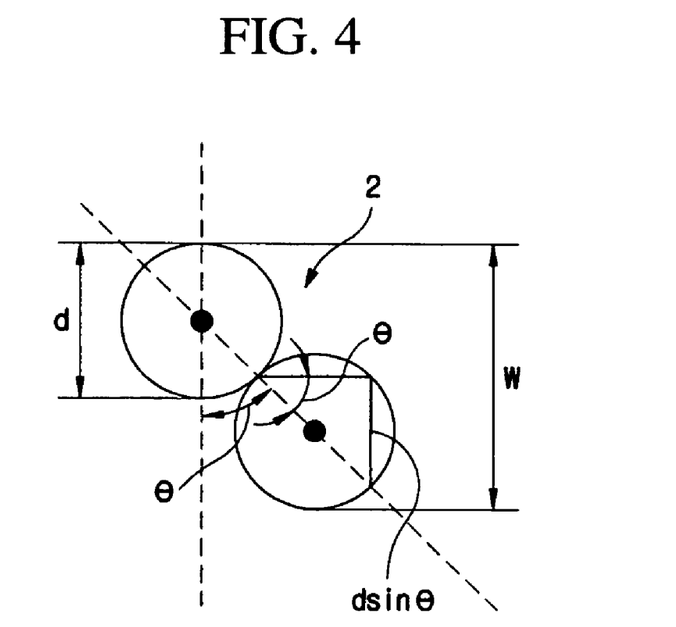
FIG. 4 is a schematic diagram for illustrating a process of calculating a width hidden by the cable according to the present invention.

Here, a width W hidden by the cable 2 may be represented as the following equation 1, when referring to FIG. 4, $$W = d \times (1 + |\sin \theta|) \qquad \text{Equation 1}$$

where d: a diameter of the wire, θ a rotation angle of the wire.

Figure 5:
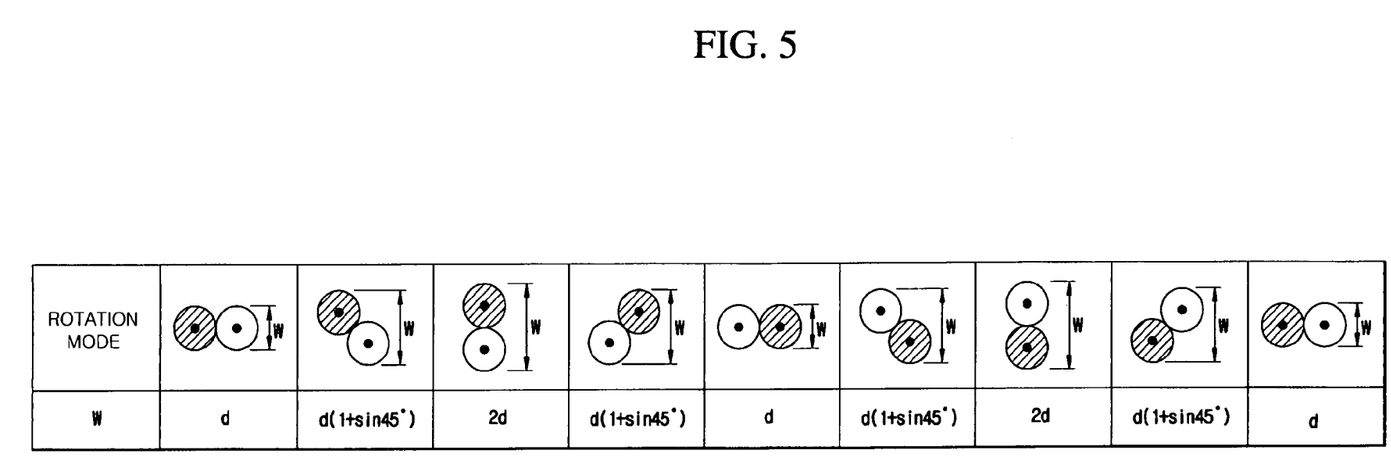
FIG. 5 is a schematic diagram showing a change of the area hidden by the cable in accordance with a rotation of a wire.

FIG. 5 illustrates a value of W and a rotation mode of the wire which are changed in accordance with movement of the cable 2, and calculated by the equation 1.

Referring to FIG. 5, when the stranded cable is interposed between the light-emitting unit 100 and the light-receiving unit 115 so as to make a value of W become d, a hidden area of a light-receiving element 115a is minimized. On the other hand, when the stranded cable is interposed between the light-emitting unit 100 and the light-receiving unit 115 so as to make a value of W become 2d, the hidden area of the light-receiving element 115a is maximized. As a result, it would be known that the light-receiving quantity is changed according to a rotation angle.

In addition, a stranded structure of the cable 2 becomes one pitch when the wire substantially returns to its original position by rotating as much as 360 degrees. However, it would be noticed that the light-receving quantity is changed as much as two cycles in one pitch.

Preferably, a lens unit 105 having a collimator function is located between the light-emitting unit 100 and the stranded cable 2. The lens unit 105 converts a ray radiated from the light-emitting unit 100 into a parallel ray, and irradiates the parallel ray toward the light-receiving unit 115. A width of the parallel ray should be set at least wider than a diameter of the cable.

In addition, an optical slit 110 for controlling a changed degree of a light quantity sensed by the light-receiving element 115a is interposed between the stranded cable 2 and the light-receiving unit 115 so as to control a signal-to-noise ratio (or, a S/N ratio) of the signal output from the light-receiving element 115a. For example, since a change of a light quantity reaching the light-receiving element 115a becomes larger as a width of the optical slit 110 is narrower than a predetermined critical value, the S/N ratio is improved and the signal is better detected.

An LED (Light Emitting Diode) having excellent optical characteristics and inexpensive than other elements, especially an infrared ray LED, is preferably adopted as a light-emitting element 100a, which composes the light-emitting unit 100. In addition, a photodiode is preferably adopted as the light-receiving element 115a, which composes the light-receiving unit 115.

The guide roller 120 rotates in accordance with the stranded cable 2 in a state that its circumsference is contacted with the stranded cable 2. At this time, an encoder 125 syncronized with the guide roller 120 for generating a predetermined number of pulses per one rotation of the guide roller is preferably installed on one side of the guide roller 120 so as to count rotation of the guide roller 120. For combination of the guide roller 120 and the encoder 125, which substantially act for measuring a moved distance (or, a velocity) of the stranded cable 2, a common tachometer or a rotary encoder may be adopted as it is.

Figure 6:
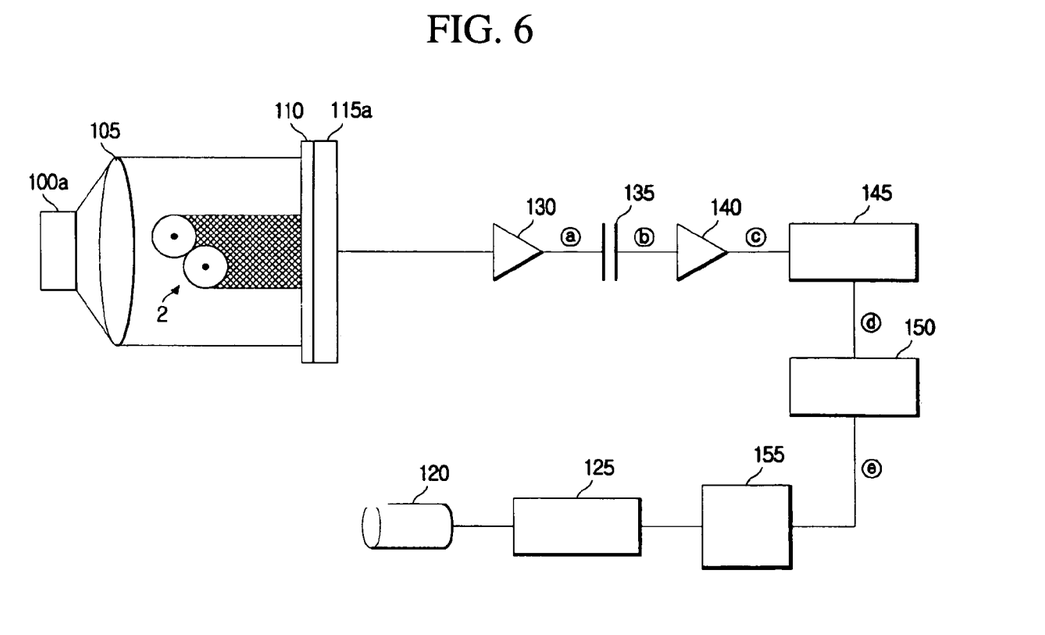
FIG. 6 is a block diagram showing functional components of the present invention.

The signal processor 155 plays a role of calculating a pitch of the spirally-stranded cable by processing a signal output from the light-receiving unit 115 and a signal related to a movement velocity of the cable, output from the encoder 125.

FIG. 6 illustrates a functional configuration of a pitch calculator for such operation of the present invention.

Referring to FIG. 6, the pitch calculator of the present invention includes a common comparator 145 for converting an electrical signal output from the light-receiving unit 115 into a square wave, a frequency divider 150 for dividing the square wave signal into two parts, and a signal processor 155 for calculating a pitch of the stranded cable by using the divided square wave signal output from the frequency divider 150 and a pulse signal output from the encoder 125.

Figure 7:
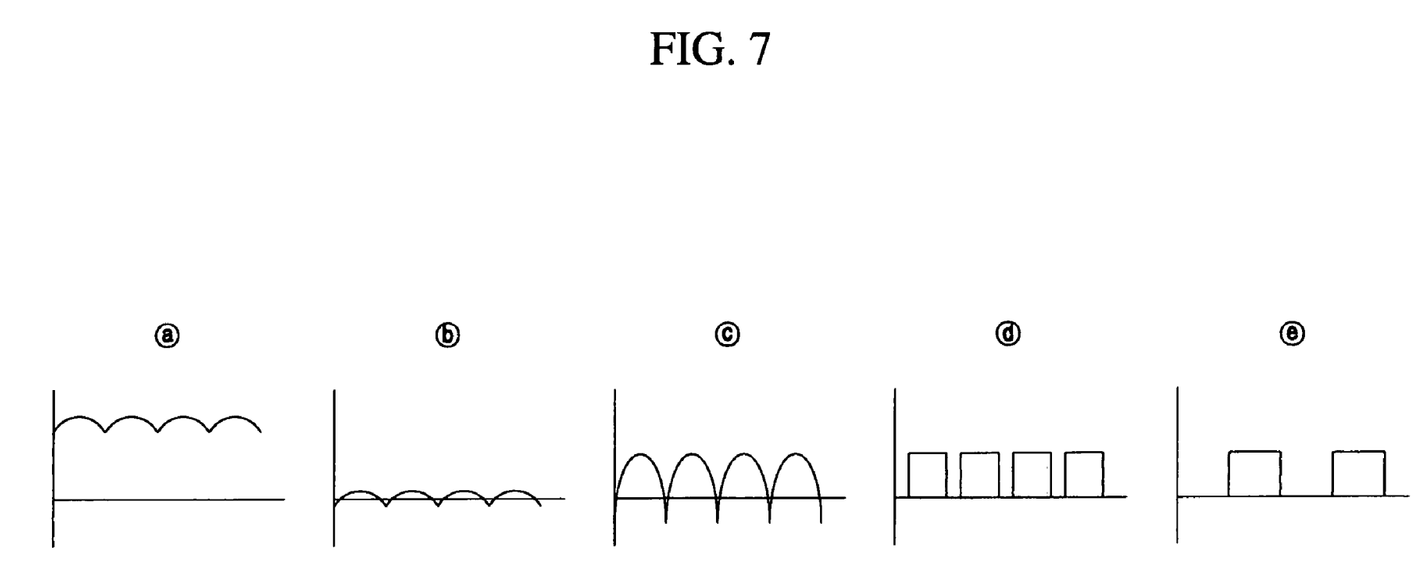
FIG. 7 is a waveform diagram of an output signal of each component in FIG. 6.

In addition, in order to generate a square wave signal, a first amplifier 130 for amplifying the light-receiving signal in a predetermined level, a condenser 135 for extracting AC components from a signal at an output of the first amplifier 130, and a second amplifier 140 for amplifying a signal at an output of the condenser 135 in a predetermined level are preferably interposed between an output of the light-receiving unit 115 and the comparator 145. Output waveforms in each component are illustrated in FIG. 7.

The square wave signal output from the comparator 145 is divided so that the two-cyclic light-receiving pattern generated during one pitch of the cable is in correspondance to one-cyclic square wave with passing through the frequency divider 150.

Figure 8:
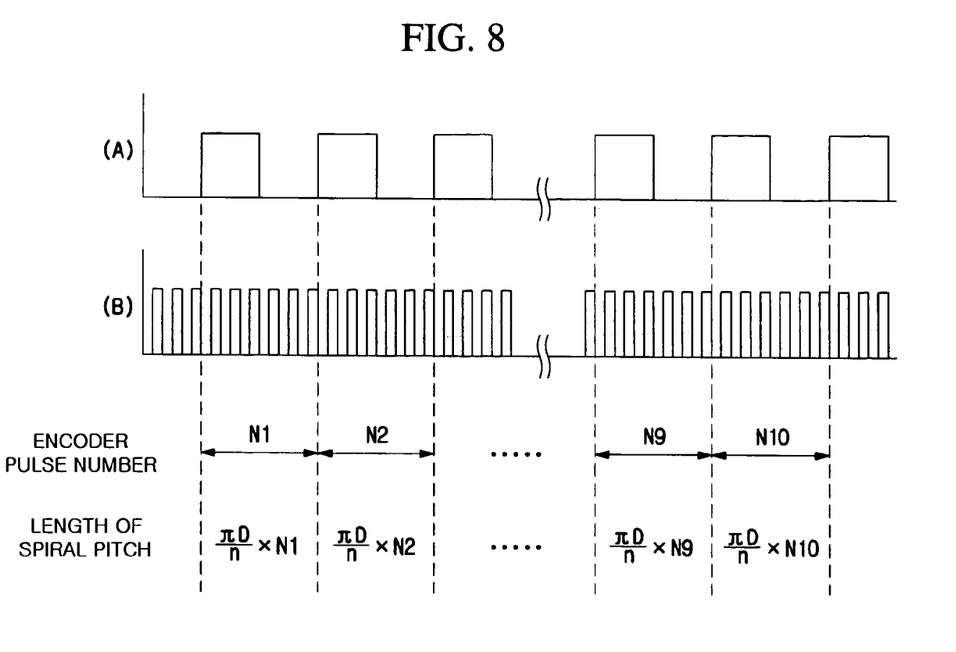
FIG. 8 is a waveform diagram of a signal for calculating a pitch of a stranded cable by using a signal processor in FIG. 6.

The signal processor 155 calculates a pitch of the stranded cable in a way of measuring a circumferential length of the guide roller 120, which is rotated per one pitch of the stranded structure, by counting the number of pulses of the encoder 125 with using the divided square wave signal as a trigger signal, as shown in FIG. 8. Accordingly, the signal processor 155 calculates a pitch P of the cable using the following equation 2.

$$P = \frac{\pi D}{n} \times N \quad \text{Equation 2}$$

where P: a stranded pitch, π: the ratio of the circumference of a circle to its diameter, D: a diameter of the guide roller, n: the number of pulses of the encoder per one rotation, and N: the number of pulses of the encoder.

By using the above equation 2, it is possible to calculate a pitch corresponding to the square wave corresponding to one cycle. If this process is repeatedly applied on each square wave, a pitch of each point of the stranded cable may be calculated in real time along a longitudinal direction of the stranded cable 2.

Hereinafter, a process of calculating a pitch of the stranded cable by using the pitch measuring apparatus according to the present invention is described in detail.

First, a device for measuring a stranded cycle of the cable 2, in which at least two wires 1 are stranded, and a device for measuring a moved distance of the cable 2 are positioned in a direction of the moving cable, as shown in FIG. 2. Here, the stranded cycle measuring device is defined to include the light-emitting unit 100 and the light-receiving unit 115 oppositely positioned with the cable interposed therebetween, and the moved distance measuring device represents the guide roller 120 and the encoder 125.

A light radiated from the light-emitting unit 100 is converted in a parallel ray having larger width than a diameter of the cable by the lens 105, and then shed on the stranded cable 2. A light-receiving quantity of the light-receiving unit 115 shows periodic patterns according to a stranded shape (or, a rotation mode) of the cable, as shown in FIG. 5.

In other words, the stranded shape of the cable periodically changes according to movement of the cable 2 positioned between the light-receiving unit 100 and the light-receiving emitting unit 115, and an output signal (i.e., the light-receiving signal) of the light-receiving receiving unit 115 accordingly has a shape of non-sinusoidal periodic wave (e.g., a full-wave rectified sinusoidal periodic wave) shown in ⓐ of FIG. 7. The light-receiving signal illustrated in ⓐ of FIG. 7 represents an amplified state by the first amplifier 130 (see FIG. 6).

The amplified light-receiving signal is input into the comparator 145 via the condensor 135 and the second amplifier 140, and then converted into a square wave signal, as shown in ⓓ of FIG. 7, by the comparator 145. The square wave signal is then converted into a divided square wave signal, as shown in ⓔ of FIG. 7, through the frequency divider 150.

On the other hand, the guide roller 120 rotates as much as a moved distance of the cable as the stranded cable 2 moves, and the encoder 125 generates pulses corresponding to the rotated distance of the guide roller 120, and inputs the pulses into the signal processor 155.

Accordingly, the signal processor 155 counts the number N of pulses of the encoder during a trigger-cycle of divided square wave signal output from the frequency divider 150, as shown in FIG. 8. A stranded pitch P of the cable may be calculated by inputting the counted pulse number N into the below equation.

$$P = \frac{\pi D}{n} \times N$$

where P: a stranded pitch, π: the ratio of the circumference of a circle to its diameter, D: a diameter of the guide roller, n: the number of pulses of the encoder per one rotation, and N: the number of pulses of the encoder.

APPLICABILITY TO THE INDUSTRY

As noted above, the present invention may compose an apparatus for measuring a pitch of a stranded cable by using an inexpensive LED, thereby saving manufacturing expenses.

In addition, since a pitch of each point of the stranded cable may be rapidly measured in real time as the stranded cable moves, it is possible to quickly deal with a stranded state of the cable.

Accordingly, if the apparatus of the present invention is used in a process for manufacturing a cable, there is an advantage that a cable having regular pitchs along a longitudinal direction may be more efficiently manufactured.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method for measuring a pitch of a stranded cable, comprising the steps of:

(a) manufacturing a stranded cable by stranding at least two wires;
(b) irradiating a parallel ray on one side of the stranded cable moving at a regular velocity, and receiving the parallel ray at the opposed side of the stranded cable; and
(c) determining a stranded cycle of the cable on the basis of a light-receiving quantity pattern on the opposed side corresponding to a stranded pattern of the cable, and then measuring a stranded pitch of the cable by calculating a moved distance of the cable during the stranded cycle.

2. The method for measuring a pitch of a stranded cable according to claim 1, wherein a width of the parallel ray irradiated on one side of the cable is set at least wider than a diameter of the cable.

3. The method for measuring a pitch of a stranded cable according to claim 1, wherein the step (c) includes the steps of:
(a) generating a light-receiving signal in a shape of non-sinusoidal periodic wave corresponding to a light-receiving quantity on the opposed side;
(b) converting the light-receiving signal into a square wave signal;
(c) dividing the square wave signal into two parts; and
(d) measuring a moved distance of the cable by using the divided square wave signal as a trigger signal.

4. The method for measuring a pitch of a stranded cable according to claim 3, wherein the light-receiving signal has a shape of full-wave rectified wave.

5. The method for measuring a pitch of a stranded cable according to claim 3, wherein the step (d) includes the steps of:
preparing a guide roller rotating in accordance with movement of the cable and an encoder for counting the rotation of the guide roller;
counting the number of pulses output from the encoder by using the divided square wave signal as a trigger signal; and
calculating a pitch P using the following equation, $$P = \frac{\pi D}{n} \times N$$

where P: a stranded pitch, π: the ratio of the circumference of a circle to its diameter, D: a diameter of the guide roller, n: the number of pulses of the encoder per one rotation, and N: the number of pulses of the encoder.

6. An apparatus for measuring a pitch of a stranded cable, comprising:
a stranded cable in which at least two wires are stranded in a predetermined pitch;
a light-emitting element and a light-receiving element positioned on both opposite sides of the stranded cable moving in a predetermined direction;
a measurement sensor for sensing a moved distance of the cable; and
a pitch calculator for calculating a pitch of the stranded cable on the basis of an output value of the measurement sensor by using periodical change of the output signal from the light-receiving element as a trigger signal.

7. The apparatus for measuring a pitch of a stranded cable according to claim 6, wherein the measurement sensor includes:
a guide roller contacted with the cable, the guide roller rotating as much as a moved distance of the cable; and
an encoder for counting the rotation of the guide roller.

8. The apparatus for measuring a pitch of a stranded cable according to claim 6, wherein the pitch calculator includes:
a comparator for converting a light quantity signal output from the light-receiving element into a square wave;
a frequency divider for dividing the square wave output from the comparator into two parts; and
a signal processor for calculating a pitch of the stranded cable by counting the number of pulses of the encoder until the divided square wave is triggered.

9. The apparatus for measuring a pitch of a stranded cable according to claim 8, wherein the signal processor calculates a pitch of the stranded cable on the basis of the following equation, $$P = \frac{\pi D}{n} \times N$$

where P: a stranded pitch, π: the ratio of the circumference of a circle to its diameter, D: a diameter of the guide roller, n: the number of pulses of the encoder per one rotation, and N: the number of pulses of the encoder.

10. The apparatus for measuring a pitch of a stranded cable according to claim 6, wherein the light-emitting element is an LED.

11. The apparatus for measuring a pitch of a stranded cable according to claim 6, wherein the light-receiving element is a photodiode.

12. The apparatus for measuring a pitch of a stranded cable according to claim 8, further comprising:
a first amplifier for amplifying the light-receiving signal between the light-receiving element and the comparator.

13. The apparatus for measuring a pitch of a stranded cable according to claim 12, further comprising:
a condensor for extracting AC component from a signal of an output of the first amplifier.

14. The apparatus for measuring a pitch of a stranded cable according to claim 13, further comprising:
a second amplifier for amplifying a signal of an output of the condenser.

* * * * *